US 6,743,955 B2

(12) United States Patent
Hiro et al.

(10) Patent No.: US 6,743,955 B2
(45) Date of Patent: Jun. 1, 2004

(54) METHOD FOR PRODUCING 2,3-DICHLORO-1-PROPANOL AND EPICHLOROHYRIN

(75) Inventors: Toshitaka Hiro, Kanagawa (JP); Kazuhiro Sakurai, Kanagawa (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 10/311,225

(22) PCT Filed: Apr. 24, 2002

(86) PCT No.: PCT/JP02/04070

§ 371 (c)(1),
(2), (4) Date: Dec. 16, 2002

(87) PCT Pub. No.: WO02/088059

PCT Pub. Date: Nov. 7, 2002

(65) Prior Publication Data

US 2003/0149311 A1 Aug. 7, 2003

Related U.S. Application Data

(60) Provisional application No. 60/291,934, filed on May 21, 2001.

(30) Foreign Application Priority Data

Apr. 26, 2001 (JP) ........................................ 2001/128670

(51) Int. Cl.$^7$ .......................... C07C 29/00; C07C 31/34
(52) U.S. Cl. ....................................... 568/850; 568/840
(58) Field of Search ................................. 568/840, 850

(56) References Cited

U.S. PATENT DOCUMENTS 4,634,784 A 1/1987 Nagato et al.

FOREIGN PATENT DOCUMENTS

| EP | 0 552 383 A1 | 7/1993 |
|---|---|---|
| JP | 59-128340 A | 7/1984 |
| JP | 59-128341 A | 7/1984 |
| JP | 03-074342 A | 3/1991 |

OTHER PUBLICATIONS

Patent Abstracts of Japan, abstracting JP–A–59–128340 of Jul. 24, 1984.
Patent Abstracts of Japan, abstracting JP–A–59–128341 of Jul. 24, 1984.
Patent Abstracts of Japan, abstracting JP–A–3–74342 of Mar. 28, 1991.
Patent Abstracts of Japan, vol. 1995, No. 05, Jun. 30, 1995 & JP 07 033698 A (Showa Denko), Feb. 3, 1995 Abstract.

*Primary Examiner*—Elvis O. Price
(74) *Attorney, Agent, or Firm*—Sughrue Mion, PLLC

(57) ABSTRACT

Methods for continuously producing 2,3-dichloro-1-propanol (2,3-DCH) and epichlorohydrin in high yields and in a stabel manner for a long time are disclosed. In a method where allyl alcohol is chorinated in a hyrochloric acid solution and the reaction solution is introduced into a degassing tower to release hydrogen chloride and 2,3-DCH is obtained from the remaining solution, the concentraton of chlorine in the reaction mixture to be introduced into the degassing tower is maintaining to 0.015 g/ml or less and/or the partial pressure of chlorine gas in the reactor immediately before the degassing tower to 0.08 MPa or less, by monitoring and/or the partial pressure of chlorine gas in the reactor immediately before the degassing tower to 0.08 MPa or less, by monitoring and/or controlling the chlorine concentration of a solution at the outlet of the reactor immediately before the degassing tower and/or the partial pressure of chlorine gas present in the gas phase section of the reactor and the flow rate of chlorine gas immediately before the degassing tower.

8 Claims, 2 Drawing Sheets

METHOD FOR PRODUCING 2,3-DICHLORO-1-PROPANOL AND EPICHLOROHYRIN

CROSS REFERENCE TO THE RELATED APPLICATIONS

This is an application based on the prescription of 35 U.S.C. Section 111(a) with claiming the benefit of filing date of U.S. Provisional application Serial No. 60/291,934 filed May 21, 2001 under the provision of 35 U.S.C.111(b), pursuant to 35 U.S.C. Section 119(e) (1).

TECHNICAL FIELD

The present invention relates to a method for producing 2,3-dichloro-1-propanol (hereinafter, sometimes abbreviated as "2,3-DCH"), which is an intermediate for the production of epichlorohydrin used as a solvent, a raw material for producing epoxy resin, a raw material for producing synthetic rubbers, a stabilizer for chlorinated rubber raw material and the like and to a method for producing epichlorohydrin (hereinafter, sometimes abbreviated as "ECH") from 2,3-DCH. The invention relates to a method for producing 2,3-dichloro-1-propanol by reacting allyl alcohol with chlorine in a hydrochloric acid solution.

BACKGROUND ART

Many proposals have been made on the production method for producing 2,3-dichloro-1-propanol (2,3-DCH) by chlorinating allyl alcohol with chlorine in a hydrochloric acid solution. In particular, it has been known that reaction of allyl alcohol with chlorine in a high concentration hydrochloric acid solution can produce 2,3-DCH in high yields (Japanese Patent Application Laid-open Nos. 59-128340, 59-128341, and 3-74342, etc.)

As an industrially useful continuous production method for 2,3-DCH, for example, Japanese Patent Application Laid-open Nos. 59-128340, 60-258171 (U.S. Pat. No. 4,634,784), and 3-74342, etc. disclose methods for the production of 2,3-DCH by introducing a solution obtained by chlorination of allyl alcohol in a hydrochloric acid solution into a degassing tower and heating the solution to release hydrogen chloride, followed by recovering the hydrogen chloride and sending it to the reactor. As for the proportions between allyl alcohol and chlorine used in these methods, Japanese Patent Application Laid-open No. 3-74342 describes supply of an excessive amount of chlorine in a range of 10 mol % or less to allyl alcohol, and Japanese Patent Application Laid-open No. 59-128340 describes that the amount of chlorine of about 1.05 mol or less per mol of allyl alcohol is sufficient.

However, in the continuous method for the production of 2,3-DCH by introducing a solution obtained by chlorination of allyl alcohol in a hydrochloric acid solution in a degassing tower and heating the solution to release hydrogen chloride, followed by recovering the hydrogen chloride and sending it to the reactor, there has been a problem in that the continued supply of chlorine in amounts more than stoichiometric proportion with respect to allyl alcohol results not only in a loss of excessively supplied chlorine but also in a reduction in the partial pressure of gas phase hydrogen chloride in the hydrogen chloride absorber and/or reactor, which in turn causes a reduction in the yield of 2,3-DCH. Conversely, the continued supply of allyl alcohol in amounts more than stoichiometric proportion with respect to chlorine will not only cause a problem of a loss of unreacted allyl alcohol but also invite clogging of the heater of the degassing tower due to accumulation of the polymer, so that the operation cannot be continued in a stable manner for a long time.

Furthermore, Japanese Patent Application Laid-open No. 3-74342 describes that the concentration of allyl alcohol in the reaction mixture that is continuously taken out of the system should be substantially zero. However, it contains no specific description as to how to make the concentration of allyl alcohol to zero.

DISCLOSURE OF THE INVENTION

Therefore, an object of the present invention is to provide a continuous method for the production of 2,3-DCH by introducing a solution obtained by chlorination of allyl alcohol in a hydrochloric acid solution into a degassing tower and heating the solution to release hydrogen chloride, followed by recovering the hydrogen chloride and sending it to the reactor, in which the concentration of allyl alcohol remaining in the reaction mixture introduced in the degassing tower is made substantially zero so that 2,3-DCH and epichlorohydrin can be continuously produced in high yields and in a stable manner for a long time.

Under the circumstance, extensive studies have been made and as a result, it has now been found that in a continuous method for the production of 2,3-DCH by introducing a solution obtained by chlorination of allyl alcohol in a hydrochloric acid solution into a degassing tower and heating it to release hydrogen chloride, followed by recovering the hydrogen chloride and sending it to the reactor, in order to make the concentration of allyl alcohol remaining in the reaction mixture introduced in the degassing tower substantially zero and continuously obtain 2,3-dichloro-1-propanol in high yields, it is necessary to control the concentration of chlorine dissolved in the reaction mixture to be introduced in the degassing tower to a specified concentration or less and/or to control the partial pressure of chlorine gas present in the gas phase section of the reactor immediately before the degassing tower to a specified partial pressure or less. It is further recognized that it is important to arrange an automatic analyzer for measuring the chlorine concentration in a solution at the outlet of the reactor immediately before the degassing tower and/or the concentration (partial pressure) of chlorine gas present in the gas phase section of the reactor as means for controlling the concentration of chlorine dissolved in the reaction mixture in the reactor immediately before the degassing tower and/or the partial pressure of the gas phase section of the reactor immediately before the degassing tower within a specified range and control the flow rate of chlorine gas to be introduced into the reactor immediately before the degassing tower in accordance with the reading of the analyzer. Thus, the present invention has been accomplished.

That is, the present invention provides methods for producing 2,3-dichloro-1-propanol and methods for producing epichlorohydrin as described below:

1) A method for producing 2,3-dichloro-1-propanol by introducing a solution containing 2,3-dichloro-1-propanol obtained by chlorination of allyl alcohol in a hydrochloric acid solution into a degassing tower to release hydrogen chloride, returning the hydrogen chloride to a reactor for the chlorination, and obtaining 2,3-dichloro-1-propanol from the remaining solution, characterized in that the method comprises maintaining the concentration of chlorine dissolved in the solution at an outlet of the reactor immediately before introduction to the degassing tower to 0.015 g/ml or less.

2) A method for producing 2,3-dichloro-1-propanol by introducing a solution containing 2,3-dichloro-1-propanol obtained by chlorination of allyl alcohol in a hydrochloric acid solution into a degassing tower to release hydrogen chloride, returning the hydrogen chloride to a reactor for the chlorination, and obtaining 2,3-dichloro-1-propanol from the remaining solution as described in 1) above, characterized in that the method comprises arranging in the reactor immediately before degassing tower an analyzer for monitoring the concentration of chlorine dissolved in the solution at an outlet of the reactor and controlling the flow rate of chlorine gas to be introduced into the reactor so that the concentration of chlorine can be maintained at 0.015 g/ml or less.

3) A method for producing 2,3-dichloro-1-propanol by introducing a solution containing 2,3-dichloro-1-propanol obtained by chlorination of allyl alcohol in a hydrochloric acid solution into a degassing tower to release hydrogen chloride, returning the hydrogen chloride to a reactor for the chlorination, and obtaining 2,3-dichloro-1-propanol from the remaining solution, characterized in that the method comprises maintaining the partial pressure of chlorine in a gas phase section in the reactor immediately before the degassing tower to 0.08 MPa (absolute pressure) or less.

4) A method for producing 2,3-dichloro-1-propanol by introducing a solution containing 2,3-dichloro-1-propanol obtained by chlorination of allyl alcohol in a hydrochloric acid solution into a degassing tower to release hydrogen chloride, returning the hydrogen chloride to a reactor for the chlorination, and obtaining 2,3-dichloro-1-propanol from the remaining solution as described in 3) above, characterized in that the method comprises arranging in the reactor immediately before degassing tower an analyzer for monitoring the concentration of chlorine gas in the gas phase section of the reactor and controlling the flow rate of chlorine gas to be introduced into the reactor so that the partial pressure of chlorine gas can be maintained 0.08 MPa (absolute pressure) or less.

5) A method for producing 2,3-dichloro-1-propanol as described in any one of 1) to 4) above, wherein a hydrochloric acid aqueous solution containing 40 to 75 mass % of hydrogen chloride as $HCl/(H_2O+HCl)$ is used.

6) A method for producing 2,3-dichloro-1-propanol as described in any one of 1) to 4) above, wherein the chlorination reaction of allyl alcohol is performed at a temperature of −30 to +20° C.

7) A method for producing 2,3-dichloro-1-propanol as described in any one of 1) to 4) above, wherein the chlorination reaction of allyl alcohol is performed at a pressure of 1 MPa (gauge pressure) or less.

8) A method for producing epichlorohydrin, characterized in that the method comprises subjecting 2,3-dichloro-1-propanol as produced in any one of 1) to 7) above to saponification reaction.

BEST MODE FOR CARRYING OUT THE INVENTION

Figure 1:
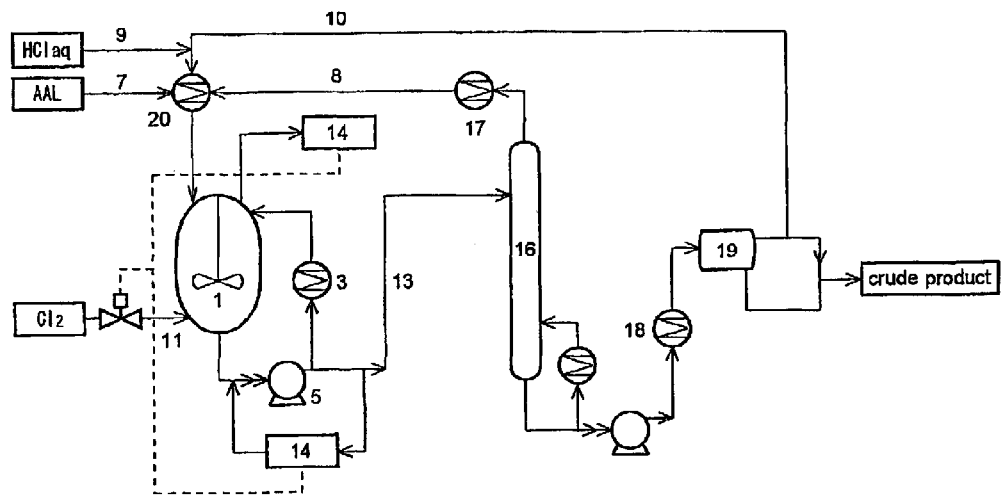
FIG. 1 is a flow chart for illustrating an embodiment of the method for the production of 2,3-dichloro-1-propanol according to the present invention using a one-stage type reaction apparatus.

Hereinafter, the present invention will be described in more detail.

Hydrochloric acid used in the present invention as a reaction solvent may be any one of 35 mass % concentrated hydrochloric acid aqueous solution, a hydrochloric acid aqueous solution obtained as an upper phase solution by degassing the reaction mixture of chlorination of allyl alcohol and cooling and then subjecting the obtained liquid to phase separation, a hydrochloric acid aqueous solution obtained in the purification step of 2,3-dichloro-1-propanol as the subsequent step and mixtures thereof. As the raw material allyl alcohol, either anhydrous one or aqueous solution may be used. The chlorine gas may be obtained by vaporization of liquid chlorine or may be one that includes about 1 to about 3% of hydrogen, air and other gases.

The hydrogen chloride gas separated in the degassing tower may be recovered and sent to the reactor or recovered by a hydrogen chloride gas absorber arranged in the preceding stage of the reactor. In a case where a hydrogen chloride gas absorber is arranged, hydrogen chloride gas can be recovered by using a reaction solvent and/or a mixed solution consisting of a reaction solvent and raw material allyl alcohol as an absorbent solution. In a case where the raw allyl alcohol is supplied to the hydrogen chloride gas absorber arranged in the preceding stage of the reactor, the temperature of absorption is preferably from −30° C. to +20° C. If it is above 20° C., by-products due to the reaction between hydrogen chloride and allyl alcohol, such as allyl chloride and 2-chloro-1-propanol increase. On the other hand, although it is advantageous for decreasing the by-products, the temperature below −30° C. is not preferable, since the viscosity of the reaction mixture increases and too much cost will be required for cooling.

Examples of the known reactor for use in the reaction between allyl alcohol and chlorine includes a stirring tank type reactor combined with an outer condenser, a wet wall type reactor that performs reaction and cooling at the same time, a tube type reactor in the form of a ring and the like. It is known that addition reaction of chlorine to allyl alcohol is very quick and the reaction will be completed at a residence time of about 30 seconds. From this, it follows that the reactor to be used in the present invention may be any reactor that can secure a residence time of 30 seconds and any one of the above-mentioned reactors may be used. The reactor may be either of one-stage type or multi-stage type.

In a case the reaction is performed in a one-stage type reaction apparatus, the reactor is provided with a chlorine concentration analyzer and the flow rate of chlorine gas to be supplied is controlled by the indication value of the arranged chlorine concentration analyzer.

In a case where the reaction is performed in a multi-stage type reaction apparatus, the reactor to which a chlorine concentration analyzer is to be arranged will differ depending on the manner of addition of a reaction solvent or a solution after absorption of hydrogen chlorine gas into the reactor. That is, when n reactors are supplied in parallel with a reaction solvent or a solution after absorption of hydrogen chloride solution and n reactor outlet solutions, respectively, or as a mixture supplied to the degassing tower, all the n reactors must be provided with chlorine concentration analyzers, respectively and the flow rate of chlorine gas to be supplied to each reactor must be controlled by the indication value of the chlorine concentration analyzer arranged therein. On the other hand, in a case where a reaction solvent or a solution after absorption of hydrogen chloride gas is supplied to n reactors in series and the outlet solution of the n-th reactor is supplied to the degassing tower, the chlorine concentration analyzer may be arranged in the n-th reactor only and the flow rate of chlorine gas to be supplied to the n-th reactor may be controlled by the indication value of the arranged chlorine concentration analyzer. The method of addition of raw material allyl alcohol may be either a lump sum supply to the above-mentioned hydrogen chloride gas absorber or a divided supply immediately before each of the n reactors.

In the case of a multi-stage type reaction apparatus using a plurality of reactors connected in parallel, the chlorine concentration analyzer must be arranged in each reactor. However, the concentration of allyl alcohol can be made substantially zero in each reactor so that by-production of allyl chloride, 2-chloro-1-propanol and the like due to side reactions between ally alcohol and hydrogen chloride can be inhibited. In contrast, the multi-stage type reaction apparatus using reactors connected in series has an advantage in that the arrangement of chlorine concentration analyzer and control of flow rate of chlorine gas may be performed only for the reactor of final stage so that operation of running the system is simple.

Hereinafter, one-stage reaction, and series- and parallel-type reactions using two reactors as representative examples of multi-stage reaction will be illustrated in detail by referring to the attached drawings.

FIG. 1 is a flow chart illustrating chlorination reaction of allyl alcohol according to the present invention using a one-stage type reaction apparatus. The chlorination reaction apparatus is constituted by a unit having a reactor 1, equipped with a stirrer, a heat exchanger 3, and a circulation pump 5, connected through pipes in the form of a ring. In a gas phase section of the reactor 1 is arranged a pipe for discharging gas phase gas to outside the system. These pipes are provided with valves, respectively. An outlet pipe of the circulation pump 5 branches into a pipe 13 for supplying to a degassing tower 16 to supply a solution to the degassing tower 16 from reactor 1. A chlorine concentration analyzer 14 is arranged in a gas extracting pipe or an extracting pipe of the circulation pump 5. The whole apparatus is well kept cool and a refrigerant is circulated in the heat exchanger to cool. An allyl alcohol introduction pipe 7, a pipe 8 for introducing hydrogen chloride gas recovered from the degassing tower, a hydrochloric acid aqueous solution introduction pipe 9, and a recovered reaction solvent introduction pipe 10 are connected to a hydrogen chloride gas absorber 20, where hydrogen chloride gas is absorbed, which is supplied to the reactor 1. In the hydrogen chloride absorber is circulated the refrigerant to cool it. A chlorine introduction pipe 11 is arranged so as to supply chlorine to the reactor 1.

The chlorine concentration analyzer 14 used in the present invention may be of any type as far as it is of analysis type as generally used in the presence of hydrochloric acid, such as an absorptiometric method and a titration method. Measured values of the chlorine concentration analyzer 14 arranged in the gas phase section or liquid phase section and the flow rate of chlorine gas supplied from the chlorine introduction pipe 11 are cascade controlled so that the flow rate of chlorine gas to be supplied to the reactor 1 can be controlled such that the partial pressure of chlorine in the gas phase section of the reactor 1 or the concentration of chlorine in the reaction mixture in the reactor 1 is constant.

The degassing tower 16 is usually a distillation tower and the overhead gas is flown through a condenser 17. The condensate is refluxed and hydrogen chloride gas is recovered in a hydrogen chloride gas absorber 20. On the bottom of the tower is arranged a heater to heat the reaction mixture. The liquid on the bottom of the degassing tower is cooled by a cooler 18 and then introduced into a separation tank 19. The separation tank 19 has a liquid supply port and upper phase and lower phase extraction ports and after standing the liquid separate it into an upper phase and a lower phase. From the upper phase a predetermined amount is extracted and is recovered to the hydrogen chloride gas absorber 20 through the introduction pipe 10. The remainder of the upper phase and the lower phase are recovered as a crude product of 2,3-dichloro-1-propanol.

Figure 2:
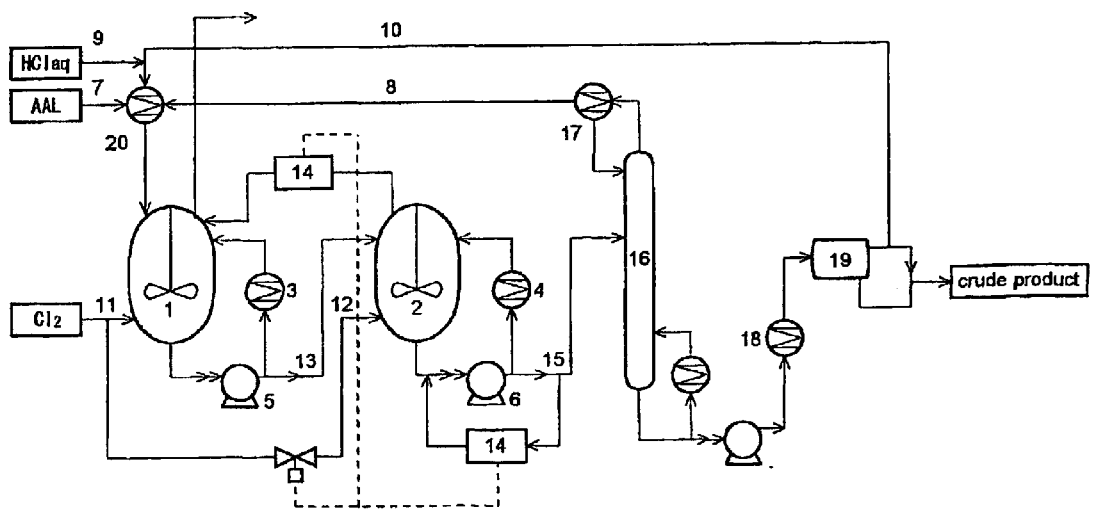
FIG. 2 is a flow chart for illustrating an embodiment of the method for the production of 2,3-dichloro-1-propanol according to the present invention using a two-stage type reaction apparatus connected in series.

FIG. 2 is a flow chart of chlorination reaction of allyl alcohol according to the present invention using a chlorination reaction apparatus having two reactors connected in series.

The chlorination reaction apparatus is constituted by a unit having reactors 1 and 2 each equipped with a stirrer, heat exchangers 3 and 4, and circulation pumps 5 and 6, connected through pipes in the form of a ring. In gas phase sections of the reactors 1 and 2 are connected to each other through a pipe. The gas phase section of the reactor 1 is provided with a pipe for discharging a gas phase gas to outside the system. These pipes are provided with valves, respectively. An outlet pipe of a circulation pump 5 branches into a pipe 13 for supplying to the reactor 2 to supply a liquid from the reactor 1 to the reactor 2. The whole apparatus is well kept cool and a refrigerant is circulated in the heat exchangers to cool. Allyl alcohol (introduction pipe 7), hydrogen chloride gas recovered from the degassing tower (introduction pipe 8), hydrochloric acid (introduction pipe 9), and a recovered reaction solvent (introduction pipe 10) are supplied to a hydrogen chloride gas absorber 20, where hydrogen chloride gas is absorbed, which is supplied to the reactor 1. In the hydrogen chloride absorber is circulated the refrigerant to cool it. Chlorine introduction pipes 11 and 12 are arranged so as to supply chlorine to the reactors 1 and 2, respectively. An outlet pipe of a circulation pump 6 branches into a pipe 15 for supplying to a degassing tower 16 and supplies a liquid from the reactor 2 to the degassing tower 16. A chlorine concentration analyzer 14 is arranged in a pipe for extracting a gas phase gas from the gas phase section of the reactor 2 to the reactor 1 or in an extraction pipe of the circulation pump 6. As the chlorine concentration analyzer 14, the above-mentioned ones may be used.

Measured values of the chlorine concentration analyzer 14 arranged in the gas phase section or liquid phase section and the flow rate of chlorine gas supplied from the chlorine introduction pipe 12 are cascade controlled so that the flow rate of chlorine gas to be supplied to the reactor 2 can be controlled such that the partial pressure of chlorine in the gas phase section of the reactor 2 or the concentration of chlorine in the reaction mixture in the reactor 2 is constant. The degassing tower 16 is usually a distillation tower and the overhead gas is flown through a condenser 17. The condensate is refluxed and hydrogen chloride gas is recovered in a hydrogen chloride gas absorber 20. On the bottom of the tower is arranged a heater to heat the reaction mixture. The liquid on the bottom of the degassing tower is cooled by a cooler 18 and then introduced into a separation tank 19. The separation tank 19 has a liquid supply port and upper phase and lower phase extraction ports, and after standing, the liquid separates into an upper phase and a lower phase. From the upper phase a predetermined amount of the liquid is extracted and is recovered to the hydrogen chloride gas absorber 20 through the introduction pipe 10. The remainder of the upper phase and the lower phase are recovered as a crude product of 2,3-dichloro-1-propanol.

Figure 3:
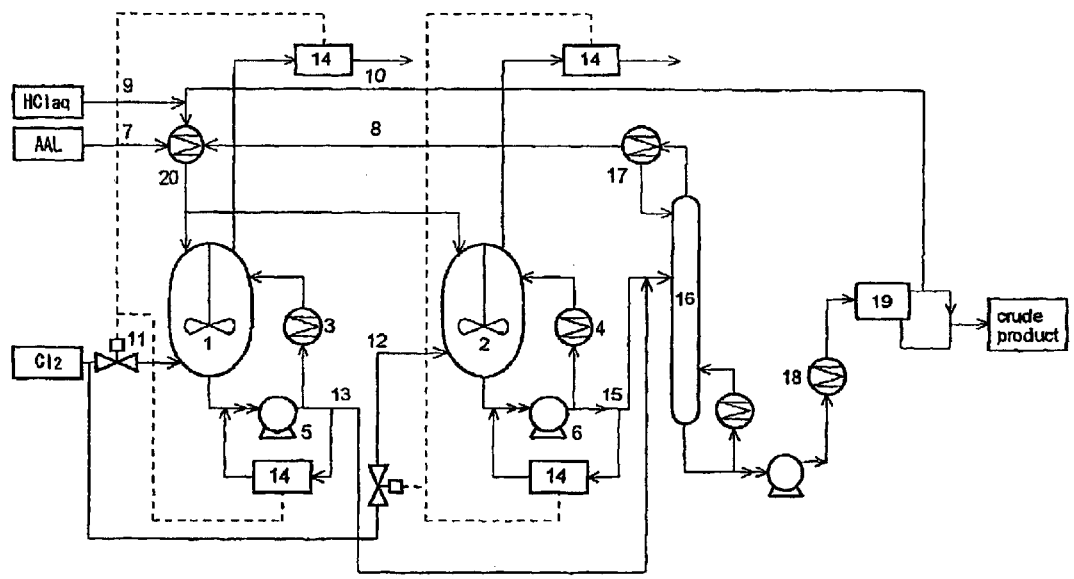
FIG. 3 is a flow chart for illustrating an embodiment of the method for the production of 2,3-dichloro-1-propanol according to the present invention using a two-stage type reaction apparatus connected in parallel.

FIG. 3 is a flow chart of chlorination reaction of allyl alcohol according to the present invention using a chlorination reaction apparatus having two reactors connected in parallel.

The chlorination reaction apparatus is constituted by a unit having reactors 1 and 2 each equipped with a stirrer, heat exchangers 3 and 4, and circulation pumps 5 and 6, connected through pipes in the form of a ring. In gas phase sections of the reactors 1 and 2 are arranged pipes for discharging a gas phase gas to outside the system. These pipes are provided with valves, respectively. Outlet pipes of circulation pumps 5 and 6 branch into pipes 13 and 15, respectively, for supplying to a degassing tower 16 and supply a liquid from the reactors 1 and 2, respectively, to the degassing tower 16. The whole apparatus is well kept cool and a refrigerant is circulated in the heat exchangers to cool. Allyl alcohol (introduction pipe 7), hydrogen chloride gas recovered from the degassing tower (introduction pipe 8), hydrochloric acid (introduction pipe 9), and a recovered reaction solvent (introduction pipe 10) are supplied to a hydrogen chloride gas absorber 20, where hydrogen chloride gas is absorbed, which is supplied to the reactors 1 and 2. In the hydrogen chloride absorber is circulated the refrigerant to cool it. Chlorine introduction pipes 11 and 12 are arranged so as to supply chlorine to the reactors 1 and 2. Chlorine concentration analyzers 14 are arranged in a pipe for extracting a gas phase gas from the gas phase section of the reactor 1 or an extraction pipe of the circulation pump 5 and in a pipe for extracting a gas phase gas from the gas phase section of the reactor 2 or an extraction pipe of the circulation pump 6. As the chlorine concentration analyzers 14, the above-mentioned ones may be used, respectively.

Measured values of the chlorine concentration analyzer 14 arranged in the gas phase section or liquid phase section of the reactor 1 and the flow rate of chlorine gas supplied from the chlorine introduction pipe 11 are cascade controlled so that the flow rate of chlorine gas to be supplied to the reactor 1 can be controlled such that the partial pressure of chlorine in the gas phase section of the reactor 1 or the concentration of chlorine in the reaction mixture in the reactor 1 is constant. Also, measured values of the chlorine concentration analyzer 14 arranged in the gas phase section or liquid phase section of the reactor 2 and the flow rate of chlorine gas supplied from the chlorine introduction pipe 12 are cascade controlled so that the flow rate of chlorine gas to be supplied to the reactor 2 can be controlled such that the partial pressure of chlorine in the gas phase section of the reactor 2 or the concentration of chlorine in the reaction mixture in the reactor 2 is constant.

The degassing tower 16 is usually a distillation tower and the overhead gas is flown through a condenser 17. The condensate is refluxed and hydrogen chloride gas is recovered in a hydrogen chloride gas absorber 20. On the bottom of the tower is arranged a heater to heat the reaction mixture. The liquid on the bottom of the degassing tower is cooled by a cooler 18 and then introduced into a separation tank 19. The separation tank 19 has a liquid supply port and upper and lower phase extraction ports, and after standing, the liquid separates into an upper phase and a lower phase. From the upper phase a predetermined amount of the liquid is extracted and is recovered to the hydrogen chloride gas absorber 20 through the introduction pipe 10. The remainder of the upper phase and the lower phase are recovered together as a crude product of 2,3-dichloro-1-propanol.

In the method of the present invention, it is necessary that chlorine be dissolved in the reactor outlet solution immediately before the degassing tower even in a small amount. However, the state in which too much chlorine is dissolved therein is not preferable. The amount of dissolved chlorine is preferably from a concentration of higher than 0 g/ml and not more than 0.015 g/ml. A concentration of higher than 0.015 g/ml is not preferable since at this concentration the chlorine dissolved in the reaction mixture accelerates the oxidation reaction from alcohol to aldehyde and the pressure of the reactor increases considerably. A more preferable concentration of chlorine is from 0.001 g/ml to 0.005 g/ml. As for the partial pressure of chlorine in the gas phase section of the reactor immediately before the degassing tower, based on the same reasons as described above, it is necessary that chlorine is present in the gas phase even in a small amount. It is preferred that chlorine is present in a chlorine partial pressure of 0.08 MPa (absolute pressure) or less and more preferably in a chlorine partial pressure of from 0.005 MPa to 0.025 MPa (absolute pressure).

In the present invention, it is preferred to use hydrochloric acid to be used as a reaction solvent in the reaction between allyl alcohol and chlorine is an aqueous solution containing hydrogen chloride in an amount of 40 to 75 mass % as $HCl/(H_2O+HCl)$. "Hydrogen chloride concentration" as defined herein also includes the amount of water to be brought by allyl alcohol as the raw material into the reaction system. Hydrogen chloride concentrations of less than 40 mass % as $HCl/(H_2O+HCl)$ are not preferable since byproducts such as 3-chloro-1,2-propandiol and ethers will increase. On the other hand, hydrogen chloride concentrations of more than 75 mass % as $HCl/(H_2O+HCl)$ are not preferable since byproducts such as allyl chloride, 2-chloro-1-propanol and 1,2,3-trichloropropane will increase. The reaction temperature is preferably 20° C. or lower since reaction temperatures above 20° C. will increase byproducts such as allyl chloride, 2-chloro-1-propanol and 1,2,3-trichloropropane. On the other hand, temperatures lower than −30° C. are not preferable since although such temperatures advantageous in improving the yield but the viscosity of the reaction mixture will increase and too much cost will be required for cooling. It is preferred to perform the reaction at a reaction pressure of from 0 to 1 MPa (gauge pressure). Reaction pressures higher than 1 MPa (gauge pressure) are not preferable since such pressures will cause an increase in the hydrogen chloride concentration, which increases byproducts such as allyl chloride, 2-chloro-1-propanol and 1,2,3-trichloropropane.

The method for the production of epichlorohydrin (ECH) according to the present invention is characterized by subjecting 2,3-dichloro-1-propanol (2,3-DCH) to saponification. Saponification reaction of 2,3-DCH may be performed after purification of 2,3-DCH.

The saponification reaction is to produce ECH by the reaction between 2,3-DCH and alkali and the reaction is performed by using 1.0 to 1.5 equivalent of alkali to 2,3-DCH. The alkali used in the saponification reaction includes, for example, $Ca(OH)_2$, NaOH, KOH, $Na_2CO_3$, $K_2CO_3$, etc. These may be used as aqueous solutions or slurry solutions.

The reaction conditions are not particularly limited. The reaction may be performed, for example, at a temperature of from 40 to 110° C. under reduced pressure or under pressure. As for the mode of reaction, various methods can be used.

BEST MODE FOR CARRYING OUT THE INVENTION

Hereinafter, the present invention will be specifically described by examples and comparative examples.

EXAMPLE 1

Figure 4:
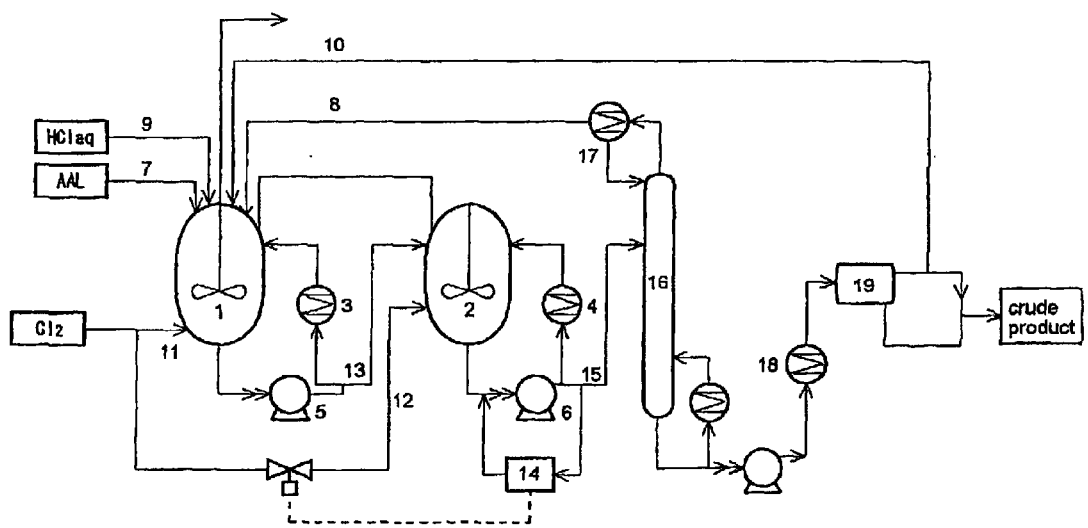
FIG. 4 is a flow chart for illustrating one embodiment of the method for the production of 2,3-dichloro-1-propanol according to the present invention using a two-stage type reactor connected in series.

Method for the Production of 2,3-DCH with Cascade Control of the Supply Amount of Chlorine Gas Chlorination reaction of allyl alcohol was performed by using a reaction apparatus having two reactors in series as shown in FIG. 4.

The apparatus shown in FIG. 4 was the same as the construction shown in the flow chart in FIG. 2 except that the hydrogen chloride gas absorber 20 was omitted and the allyl alcohol introduction pipe 7, introduction pipe 8 for hydrogen chloride gas recovered from the degassing tower, introduction pipe 9 for hydrochloric acid solution and introduction pipe 10 for recovered reaction solvent are directly supplied to the reactor 1 without passing through the hydrogen chloride gas absorber 20.

The chlorine concentration analyzer 14 was arranged only to the extraction pipe of the circulation pump 6 and the measured value of chlorine concentration in the liquid section and the flow rate of chlorine gas supplied from the chlorine introduction pipe 12 were cascade controlled and the flow rate of chlorine gas to be supplied to the reactor 2 was controlled so that the chlorine concentration in the reaction mixture in the reactor 2 could be made constant. The partial pressure of chlorine in the gas phase section was measured by a manual analysis.

As the reactors 1 and 2, 300-liter capacity glass-lined reactors each equipped with a stirrer were used, respectively. As the heat exchangers 3 and 4, graphite-made heat exchangers each having a heat transmission area of 20 m$^2$ were used. The chlorine concentration analyzer 14 used was XT-1315 (trade name, manufactured by Denki Kagaku Keiki Co., Ltd.) that measured chlorine by an amperometric titration method.

A graphite-made distillation tower filled with ceramic-made interlock saddles as the degassing tower 16 was used and overhead gas was passed through a graphite-made condenser 17 and the condensate was refluxed to recover hydrogen chloride gas in the reactor 1. The bottom of the tower was heated with steam from the graphite-made heater. The liquid on the bottom of the degassing tower was cooled by a cooler 18 and then introduced into a separation tank 19 of a 300-liter capacity glass-lined vessel. The separation tank 19 has a liquid supply port and upper and lower phase extraction ports and in the separation tank, the liquid is left to stand to separate into upper and lower phases. From the separated upper phase, a predetermined amount of the liquid was extracted and recovered in the reactor 1 through the introduction pipe 10 and the reminder of the upper phase and the lower phase were used as crude product of 2,3-dichloro-1-propanol.

Using the above-mentioned reaction apparatus, the reactor 1 was supplied with a 70 mass % allyl alcohol aqueous solution at a rate of 16.0 kg/hr from the pipe 7, a 35 mass % hydrochloric acid aqueous solution at a rate of 5.0 kg/hr from the pipe 9, a recovered reaction solvent containing 21 mass % of 2,3-dichloro-1-propanol, 60 mass % of water and 16 mass % of hydrogen chloride at a rate of 25.0 kg/hr from the pipe 10, recovered hydrogen chloride gas at a rate of 22.4 kg/hr from the pipe 8, and chlorine gas at a rate of 6.8/hr from the pipe 8. The flow rate of chlorine gas supplied to the reactor 1 was set to 50 mol % with respect to allyl alcohol. The reactor 1 was controlled so that the reaction pressure was 0.10 MPa (gauge pressure) and reaction temperature was 0° C. The reaction mixture in the reactor 1 was extracted from the pipe 13 at a rate of 75.3 kg/hr and supplied to the reactor 2. On this occasion, the reaction mixture contained 37 mass % of hydrogen chloride and 31 mass % of water, with HCl/(H$_2$O+HCl) occupying about 55 mass %. To the reactor 2 was supplied chlorine gas from the pipe 12 such that the indication value of the chlorine concentration analyzer 14 was from 0.002 to 0.004 g/ml. On this occasion, the partial pressure of chlorine in the gas phase section of the reactor 2 was from 0.01 to 0.02 MPa (absolute pressure). The reactor 2 was controlled such that the reaction pressure was 0.13 MPa (gauge pressure) and the reaction temperature was 0° C. The reaction mixture was extracted from the pipe 15 at a rate of 82.1 kg/hr and supplied to the degassing tower 16. The degassing tower 16 was run at an overhead pressure of 0.11 MPa (gauge pressure) and a tower bottom temperature of 130° C. and a gas consisting substantially of hydrogen chloride was extracted from the top of the tower at a rate of 22.4 kg/hr and introduced into the reactor 1 through the pipe 8. The tower bottom composition was extracted from the bottom of the tower at a rate of 59.7 kg/hr and cooled in the cooler 18 to about 25° C. and then introduced into the separation tank 19. After standing in the separation tank, the separated upper phase (water phase) was extracted at a rate of 28.1 kg/hr, 25.0 kg/hr out of which was introduced into the reactor 1. The remainder of the upper phase was combined with the lower phase (oil phase) to obtain a crude product at a rate of 36.6 kg/hr. Analysis of the crude product by liquid chromatography indicated that 2,3-dichloro-1-propanol was produced at 23.4 kg/hr out of the crude product and the yield was 94% based on the supplied allyl alcohol.

Under the above-mentioned reaction conditions, continuous operation was performed for 30 days but the yield of 2,3-dichloro-1-propanol did not change and no clogging of the heater of the degassing tower occurred. The molar ratio of the sum of chlorine gas supplied to the reactors 1 and 2 to the amount of the allyl alcohol supplied to the reactor 1 varied in a range of from 0.99 to 1.01.

EXAMPLE 2

Method for the Production of 2,3-DCH with Cascade Control of the Supply Amount of Chlorine Gas Chlorination reaction of allyl alcohol was performed using the reaction apparatus shown in FIG. 4 in the same manner as in Example 1. To the reactor 1 was supplied a 70 mass % allyl alcohol aqueous solution at a rate of 16.0 kg/hr from the pipe 7, a 35 mass % hydrochloric acid aqueous solution at a rate of 5.0 kg/hr from the pipe 9, a recovered reaction solvent containing 21 mass % of 2,3-dichloro-1-propanol, 60 mass % of water and 16% of hydrogen chloride at a rate of 25.0 kg/hr from the pipe 10, a recovered hydrogen chloride gas at a rate of 17.3 kg/hr from the pipe 8, and chlorine gas at a rate of 6.8 kg/hr from the pipe 11. The flow rate of chlorine gas supplied to the reactor 1 was set to 50 mol % with respect to allyl alcohol. The reactor 1 was controlled so that the reaction pressure was 0 MPa (gauge pressure) and reaction temperature was 0° C. The reaction mixture in the reactor 1 was extracted from the pipe 13 at a rate of 70.1 kg/hr and supplied to the reactor 2. On this occasion, the reaction mixture contained 33 mass % of hydrogen chloride and 33 mass % of water, with HCl (H$_2$O+HCl) occupying about 50 mass %. To the reactor 2 was supplied chlorine gas from the pipe 12 such that the indication value of the chlorine concentration analyzer 14 was from 0.002 to 0.004 g/ml. On this occasion, the partial pressure of chlorine in the gas phase section of the reactor 2 was from 0.01 to 0.02 MPa (absolute pressure). The reactor 2 was controlled such that the reaction pressure was 0.03 MPa (gauge pressure) and the reaction temperature was 0° C. The reaction mixture was extracted from the pipe 15 at a rate of 77.0 kg/hr and supplied to the degassing tower 16. The degassing tower 16 was run at an overhead pressure of 0.01 MPa (gauge pressure) and a tower bottom temperature of 120° C. and a gas consisting substantially of hydrogen chloride was extracted from the top of the tower at a rate of 17.3 kg/hr and introduced into the reactor 1 through the pipe 8. The tower bottom composition was extracted from the bottom of the tower at a rate of 59.7 kg/hr and cooled in the cooler 18 to about 25° C. and then introduced into the separation tank 19. After standing in the separation tank, the separated upper phase (water phase) was extracted at a rate of 28.6 kg/hr, 25.0 kg/hr out of which was introduced into the reactor 1. The remainder of the upper phase was combined with the lower phase (oil phase) to obtain a crude product at a rate of 34.7 kg/hr. Analysis of the crude product by liquid chromatography indicated that 2,3-dichloro-1-propanol was produced at 23.2 kg/hr out of the crude product and the yield was 93.5% based on the supplied allyl alcohol.

Under the above-mentioned reaction conditions, continuous operation was performed for 30 days but the yield of 2,3-dichloro-1-propanol did not change and no clogging of the heater of the degassing tower occurred. The molar ratio of the sum of chlorine gas supplied to the reactors 1 and 2 to the amount of the allyl alcohol supplied to the reactor 1 varied in a range of from 0.99 to 1.01.

COMPARATIVE EXAMPLE 1
Method for the Production of 2,3-DCH by Supplying Chlorine Gas in an Amount Slightly Excessive with Respect to Allyl Alcohol without Cascade Control Chlorination reaction of allyl alcohol was performed by using the same reaction apparatus as that used in Example 1 except that the cascade control of measured values of the chlorine concentration analyzer 14 and the flow rate of chlorine introduced from the pipe 12 in Example 1 was not performed. The flow rate of chlorine gas supplied to the reactors 1 and 2 was controlled to about 1.02 mole equivalent with respect to the supply amount of ally alcohol. The chlorination reaction was initiated under the conditions described below. To the reactor 1 was supplied a 70 mass % allyl alcohol aqueous solution at a rate of 16.0 kg/hr from the pipe 7, a 35 mass % hydrochloric acid aqueous solution at a rate of 5.0 kg/hr from the pipe 9, a recovered reaction solvent containing 21 mass % of 2,3-dichloro-1-propanol, 60 mass % of water and 16% of hydrogen chloride at a rate of 25.0 kg/hr from the pipe 10, and chlorine gas at a rate of 7.0 kg/hr from the pipe 11. From the pipe 8, a recovered hydrogen chloride gas was supplied to the reactor 1. The flow rate of chlorine gas supplied to the reactor 1 was set to 50 mol % with respect to the total amount of the supplied chlorine gas. The reactor 1 was controlled so that the reaction pressure was 0 MPa (gauge pressure) and reaction temperature was 0° C. The reaction mixture in the reactor 1 was extracted through the pipe 13 such that the level of the liquid in the reactor 1 was constant and supplied to the reactor 2. The reactor 2 was supplied with chlorine gas from the pipe 12 at 7.0 kg/hr in the same manner as in the case of the reactor 1. The reactor 2 was controlled such that the reaction pressure was 0.03 MPa and (gauge pressure) and the reaction temperature was 0° C. The reaction mixture was extracted from the reactor 2 through the pipe 15 such that the level of the liquid in the reactor 2 was constant and supplied to the degassing tower 16. The degassing tower 16 was run at an overhead pressure of 0.01 MPa (gauge pressure) and a tower bottom temperature of 125° C. and a gas consisting substantially of hydrogen chloride was extracted from the top of the tower and introduced into the reactor 1 through the pipe 8. The tower bottom composition was extracted from the bottom of the tower and cooled in the cooler 18 to about 25° C. and then introduced into the separation tank 19. After standing in the separation tank, 25.0 kg/hr out of the separated upper phase (water phase) was introduced into the reactor 1. The remainder of the upper phase was combined with the lower phase (oil phase) to obtain a crude product.

Continuous reaction under the above-mentioned conditions resulted in that from the pipe coupling the gas phase sections of the reactors 1 and 2 and the pipe 8, excessively supplied chlorine gas flew into the reactor 1 and after the reaction conditions became stable, chlorine gas flew out to outside the system at a rate of 0.2 kg/hr through the pipe for discharging chlorine gas from the gas phase section to the outside. This amount of chlorine corresponded to 1.4% of the sum of the amounts of chlorine supplied to the reactors. On this occasion, the concentration of chlorine dissolved in the reaction mixture in the reactor 2 was 0.018 g/ml and the partial pressure of chlorine present in the gas phase section of the reactor 2 was 0.09 MPa (absolute pressure). Analysis of the crude product by liquid chromatography indicated that 2,3-dichloro-1-propanol was produced at 22.1 kg/hr out of the crude product and the yield was 89% based on the supplied allyl alcohol.

COMPARATIVE EXAMPLE 2
Method for the Production of 2,3-DCH by Supplying Chlorine Gas in an Amount Slightly Deficient with Respect to Allyl Alcohol without Cascade Control Chlorination reaction of allyl alcohol was performed by using the same reaction apparatus as that used in Example 1 except that the cascade control of measured values of the chlorine concentration analyzer 14 and the flow rate of chlorine introduced from the pipe 12 in Example 1 was not performed. The flow rate of chlorine gas supplied to the reactors 1 and 2 was controlled to about 0.98 mol equivalent with respect to the supply amount of ally alcohol. To the reactor 1 was supplied a 70 mass % allyl alcohol aqueous solution at a rate of 16.0 kg/hr from the pipe 7, a 35 mass % hydrochloric acid aqueous solution at a rate of 5.0 kg/hr from the pipe 9, a recovered reaction solvent containing 21 mass % of 2,3-dichloro-1-propanol, 0 mass % of water and 16% of hydrogen chloride at a rate of 25.0 kg/hr from the pipe 10, a recovered hydrogen chloride gas at a rate of 17.3 kg/hr from the pipe 8, and chlorine gas at a rate of 6.7 kg/hr from the pipe 11. The flow rate of chlorine gas supplied to the reactor 1 was set to 50 mol % with respect to the total amount of the supplied chlorine gas. The reactor 1 was controlled so that the reaction pressure was 0 MPa (gauge pressure) and reaction temperature was 0° C. The reaction mixture in the reactor 1 was extracted through the pipe 13 at a rate of 70.0 kg/hr and supplied to the reactor 2. On this occasion the reaction mixture contained 33 mass % of hydrogen chloride and 33 mass % of water, with HCl/(H$_2$O+HCl) occupying about 50 mass %. The reactor 2 was supplied with chlorine gas from the pipe 12 at 6.7 kg/hr in the same manner as in the case of the reactor 1. On this occasion, the partial pressure of chroline present in the gas phase section of the reactor 2 was 0 MPa (absolute pressure) and the concentration of chlorine in the reaction mixture in the reactor 2 was 0.0 g/ml. The reactor 2 was controlled such that the reaction pressure was 0.03 MPa and (gauge pressure) and the reaction temperature was 0° C. The reaction mixture was extracted from the reactor 2 through the pipe 15 at a rate of 76.7 kg/hr and supplied to the degassing tower 16. The supplied liquid contained 0.2 kg/hr of allyl alcohol, which amount corresponded to 1.8% of the sum of the amounts of allyl alcohol supplied to the reactors. The degassing tower 16 was run at an overhead pressure of 0.01 MPa (gauge pressure) and a tower bottom temperature of 120° C. and a gas consisting substantially of hydrogen chloride was extracted from the top of the tower at a rate of 17.3 kg/hr and introduced into the reactor 1 through the pipe 8. The tower bottom composition was extracted from the bottom of the tower at a rate of 59.4 kg/hr and cooled in the cooler 18 to about 25° C. and then introduced into the separation tank 19. After standing in the separation tank, the separated upper phase (water phase) was extracted at a rate of 28.9 kg/hr, 25.0 kg/hr out of which was introduced into the reactor 1. The remainder of the upper phase was combined with the lower phase (oil phase) to obtain a crude product at a rate of 34.5 kg/hr. Analysis of the crude product by liquid chromatography revealed that 2,3-dichloro-1-propanol was produced at 22.7 kg/hr out of the crude product and the yield was 91% based on the supplied allyl alcohol.

Continuous reaction under the above-mentioned conditions resulted in that after 10 days the thermal efficiency of the heater began to decrease and examination of the heater after 20 days by stopping the reaction indicated about 60% clogging of the tubes of the heater with the polymerisate.

Industrial Applicability

According to the present invention, in the method for continuously producing 2,3-dichloro-1-propanol by introducing a solution containing 2,3-dichloro-1-propanol obtained by chlorination of allyl alcohol in a hydrochloric acid solution into a degassing tower with heating to release hydrogen chloride, returning the hydrogen chloride to a reactor for the chlorination, and obtaining 2,3-dichloro-1-propanol from the remaining solution, the concentration of allyl alcohol remaining in the reaction mixture introduced in the degassing tower can be made substantially zero and 2,3-DCH and epichlorohydrin can be continuously produced in high yields and in a stable manner for a long time by controlling the concentration of chlorine dissolved in the reaction mixture to be introduced into the degassing tower to a specified concentration (0.015 g/ml) or less, and/or controlling the partial pressure of chlorine in the gas phase section of the reactor immediately before the degassing tower to a specified partial pressure (0.08 MPa (absolute pressure)) or less, and further, by arranging an analyzer for measuring the chlorine concentration of a solution at the outlet of the reactor immediately before the degassing tower and/or the concentration (partial pressure) of chlorine gas present in the gas phase section of the reactor as means for controlling the concentration of chlorine dissolved in the reaction mixture in the reactor immediately before the degassing tower and/or the partial pressure of the gas phase section of the reactor immediately before the degassing tower within a necessary range and control the flow rate of chlorine gas to be introduced into the reactor immediately before the degassing tower in accordance with the indication value of the analyzer.

What is claimed is:

1. A method for producing 2,3-dichloro-1-propanol by introducing a solution containing 2,3-dichloro-1-propanol obtained by chlorination of allyl alcohol in a hydrochloric acid solution into a degassing tower to release hydrogen chloride, returning the hydrogen chloride to a reactor for the chlorination, and obtaining 2,3-dichloro-1-propanol from the remaining solution, characterized in that the method comprises maintaining the concentration of chlorine dissolved in the solution at an outlet of the reactor immediately before introduction to the degassing tower to 0.015 g/ml or less.

2. A method for producing 2,3-dichloro-1-propanol by introducing a solution containing 2,3-dichloro-1-propanol obtained by chlorination of allyl alcohol in a hydrochloric acid solution into a degassing tower to release hydrogen chloride, returning the hydrogen chloride to a reactor for the chlorination, and obtaining 2,3-dichloro-1-propanol from the remaining solution as described in claim 1, characterized in that the method comprises arranging in the reactor immediately before the degassing tower an analyzer for monitoring the concentration of chlorine dissolved in the solution at an outlet of the reactor and controlling the flow rate of chlorine gas to be introduced into the reactor so that the concentration of chlorine can be maintained at 0.015 g/ml or less.

3. A method for producing 2,3-dichloro-1-propanol by introducing a solution containing 2,3-dichloro-1-propanol obtained by chlorination of allyl alcohol in a hydrochloric acid solution into a degassing tower to release hydrogen chloride, returning the hydrogen chloride to a reactor for the chlorination, and obtaining 2,3-dichloro-1-propanol from the remaining solution, characterized in that the method comprises maintaining the partial pressure of chlorine in a gas phase section in the reactor immediately before the degassing tower to 0.08 MPa (absolute pressure) or less.

4. A method for producing 2,3-dichloro-1-propanol by introducing a solution containing 2,3-dichloro-1-propanol obtained by chlorination of allyl alcohol in a hydrochloric acid solution into a degassing tower to release hydrogen chloride, returning the hydrogen chloride to a reactor for the chlorination, and obtaining 2,3-dichloro-1-propanol from the remaining solution as described in claim 3, characterized in that the method comprises arranging in the reactor immediately before the degassing tower an analyzer for monitoring the concentration of chlorine gas in the gas phase section of the reactor and controlling the flow rate of chlorine gas to be introduced into the reactor so that the partial pressure of chlorine gas can be maintained 0.08 MPa (absolute pressure) or less.

5. A method for producing 2,3-dichloro-1-propanol as claimed in any one of claims 1 to 4, wherein a hydrochloric acid aqueous solution containing 40 to 75 mass % of hydrogen chloride as $HCl/(H_2O+HCl)$ is used.

6. A method for producing 2,3-dichloro-1-propanol as described in any one of claims 1 to 4, wherein the chlorination reaction of allyl alcohol is performed at a temperature of −30 to +20° C.

7. A method for producing 2,3-dichloro-1-propanol as described in any one of claims 1 to 4, wherein the chlorination reaction of allyl alcohol is performed at a pressure of 1 MPa (gauge pressure) or less.

8. A method for producing epichlorohydrin, characterized in that the method comprises subjecting 2,3-dichloro-1-propanol as produced in any one of claims 1 to 4 to saponification reaction.

\* \* \* \* \*